United States Patent [19]

Kaneoya et al.

[11] Patent Number: 4,971,909
[45] Date of Patent: Nov. 20, 1990

[54] PROCESS FOR PRODUCING OPTICALLY ACTIVE COMPOUNDS HAVING PYRIDINE SKELETONS

[75] Inventors: Masakazu Kaneoya, Kawasaki; Naoyuki Yoshida, Yokohama; Manabu Uchida, Kawasaki, all of Japan

[73] Assignee: Chisso Corporation, Osaka, Japan

[21] Appl. No.: 227,248

[22] Filed: Aug. 2, 1988

[30] Foreign Application Priority Data

Aug. 28, 1987 [JP] Japan .................................. 62-212674

[51] Int. Cl.$^5$ .............................................. C12P 17/12
[52] U.S. Cl. ...................................... 435/280; 435/122
[58] Field of Search .................................. 435/122, 280

[56] References Cited

U.S. PATENT DOCUMENTS 4,568,641 2/1986 Bewick .............................. 435/122

OTHER PUBLICATIONS

Zaks et al., Chem. Abst., vol. 103 (1985), p. 2819t.

Primary Examiner—Sam Rosen
Attorney, Agent, or Firm—Wenderoth, Lind & Ponack

[57] ABSTRACT

The present invention provides a process for producing optically active compounds by a biochemical method in which specific compounds having pyridine skeletons and hydroxyl groups are reacted with esters in the presence of hydrolases.

The compounds have the following general formula:

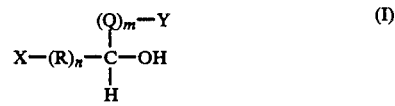

(I)

wherein X is selected from substituted pyridyl groups. Y is selected from hydrogen and halogen atoms, a cyano group, and a trifluoromethyl group. R is an alkylene group having 1-20 carbon atoms, and n is 0 or 1. Q is an alkylene group having 1-20 carbon atoms and m is 0 or 1.

17 Claims, No Drawings

PROCESS FOR PRODUCING OPTICALLY ACTIVE COMPOUNDS HAVING PYRIDINE SKELETONS

Background of the Invention

The present invention relates to a process for producing optically active compounds by a biochemical technique.

Compounds represented by the general formula:

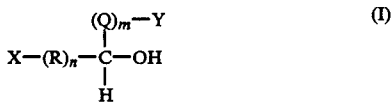

have optical isomers. In formula I, X is selected from groups of the following formula:

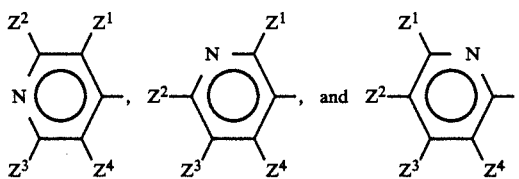

wherein each of $Z^1$, $Z^2$, $Z^3$ and $Z^4$ is selected from hydrogen and halogen atoms, a cyano group, a trifluoromethyl group, an amino group, alkylamino group, alkyl and alkoxy groups having 1-20 carbon atoms, and groups of the following formula:

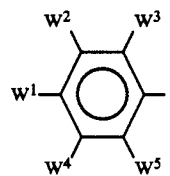

wherein each of $W^1$, $W^2$, $W^3$, $W^4$ and $W^5$ is selected from hydrogen and halogen atoms, a cyano group, a trifluoromethyl group, an amino group, alkylamino groups, and alkyl and alkoxy groups having 1-20 carbon atom, Y is selected from hydrogen and halogen atoms, a cyano group, and a trifluoromethyl group; R is an alkylene group having 1-20 carbon atoms; n is 0 or 1; Q is an alkylene group having 1-20 carbon atoms; and m is 0 or 1. Unless these compounds contain purely either the R- or S-compound in many cases they do not sufficiently exhibit their physiological activity or useful characteristics as materials for pharmaceuticals, agricultural chemicals, liquid crystal compounds and the like.

In order to obtain an optically active substance, it is necessary to optically resolve a racemate typically obtained by a synthetic chemical technique, to conduct an asymmetric synthesis, or to convert from an optically active starting material by a stereochemical synthetic method. In many cases, the process is troublesome and disadvantageous industrially.

Accordingly, it is desired to develop a technique for obtaining optically active compounds by an industrially advantageous method.

As a known biochemical technique, for example, there is a method described in Japanese Publication of Unexamined patent application No. 59-205989 in which a racemic ester is hydrolyzed with a lipase and a desired alcohol is obtained. In this case, the ester of the substrate is often insoluble in water, so that it is necessary to emulsify or stir vigorously by using a large quantity of water. Furthermore, as the enzyme is water-soluble and unstable to moisture, immobilized enzyme is required so as to act stably and to be easily removed or reused after the reaction.

Klibanov et al. reported a method in which enzyme powder was directly added into a reaction system (J. Am. Chem. Soc., 107, 7072(1985)). In this case, esters for transesterification are extremely limited and 2,2,2-trichloroethyl butyrate is used as the ester. Furthermore, it is essential to use an organic solvent, such as heptane, and ether which has many problems when it is used industrially.

Summary of the Invention

The inventors of the present invention carried out research for obtaining a process for producing optically active compounds represented by the above general formula (I) by an advantageous industrial method. They found that racemic compounds of raw materials can be efficiently resolved to optically active esters and their antipodes, by a biochemical transesterification reaction.

Namely, the present invention provides a process for producing optically active compounds which comprises using a hydrolase, reacting the (R,S)-compound represented by the above general formula (I) and an ester to perform a transesterification reaction under substantially anhydrous conditions, and resolving to an optically active compound which contains richly either the R- or S-compound and correspondingly the ester of the S- or R-compound.

According to the method of the present invention in comparison with conventional methods, the reaction is conducted under anhydrous conditions. This method does not require the use of a small amount of water or a lower alcohol instead of the water, and a side reaction does not occur such as hydrolysis of the obtained esters and esters of starting compound and formation of undesirable esters, so that the enzyme is stably kept in organic solvent and easily separated after the reaction and re-used. Furthermore, as the enzyme is directly used and reacted in organic solvent, the method can be kept free from contamination by unwanted micro-organisms. Accordingly, there is no necessity for preparing special equipment, antiseptics, sterilization treatment, etc. It is possible to conduct the reaction in an open system. Further, the reaction may be conducted in the same or less quantity of solvent in comparison with common organic synthetic reactions in high substrate concentration.

The following description illustrates this invention more specifically.

In this invention, the (R,S)-compounds of the raw materials are compounds which are available or can be synthesized easily.

It is also enough to use esters, preferably triglycerides, which are commercially available without any difficulty. Triacetin, tripropionin, tributyrin tristearin, trilaurin, trimyristin, triolein, etc., can be exemplified as the triglycerides. As for other esters, methyl propionate, ethyl butyrate, ethyl stearate, trichloroethyl laurate, butyl laurate, ethylene glycol diacetate, etc, can be used.

As the hydrolase which is used in this invention has the ability to catalyse a transesterification reaction preferentially between the R- or S-alcohol and the ester when the enzyme is used with the (R,S)-alcohol, and the enzyme can be used regardless its class. For example, a lipase, lipoprotein lipase, esterase, etc. are preferable. The following table shows commercially available enzymes that can be used in the present reaction.

TABLE

| Trade name | Origin | Seller or Maker |
| --- | --- | --- |
| Lipase AP | Aspergillus niger | Amano Pharmaceutical Co., Ltd |
| Lipase M | Mucor javanicus | Amano Pharmaceutical Co., Ltd |
| Lipase P | Pseudomonas fluorescens | Amano Pharmaceutical Co., Ltd |
| Lipase CES | Pseudomonas sp | Amano Pharmaceutical Co., Ltd |
| Lipase CE | Humicola lanuginosa | Amano Pharmaceutical Co., Ltd |
| Lipase F-AP | Rhizopus javanicus | Amano Pharmaceutical Co., Ltd |
| Lipase II | Porcine pancreas | Sigma Chemical Co., Ltd |
| Lipase VIII | Geotrichum candidum | Sigma Chemical Co., Ltd |
| Lipase X | Rhizopus delamar | Sigma Chemical Co., Ltd |
| Lipase | Chromobacterium viscosum | Toyo Jozo Co., Ltd |
| Palatase A | Aspergillus niger | Novo Industi A/S |
| Lipase | Rhizopus niveus | Nagase Biochemicals, Co. Ltd |

In addition to these enzymes, microorganisms which produce the enzymes having the above ability can be used regardless of their species and genus. As such microorganisms, the genera Arthrobacter, Acromobacter, Alcaligenes, Aspergillus, Chromobacterium, Candida, Mucor, Pseudomonas, Rhizopus, etc, can be exemplified. The enzymes produced from these miorganisms can be also used.

In the practice of the present invention, (R,S)-compounds and esters such as triglycerides can be used without any particular treatments.

The reaction is typically conducted by mixing an (R,S)-compound with an ester, preferably a triglyceride, (when the compound is slightly soluble in the ester, an organic solvent such as heptane or toluene is added), and contacting efficiently the mixture with an enzyme.

The reaction temperature is suitably 20° to 70° C. and especially preferably 30° to 45° C. The reaction time is widely variable, say 5 to 2000 hours. The reaction time can be shortened by elevating the reaction temperature or using an enzyme having high activity or lowering the substrate concentration.

The (R,S)-alcohol which is a substrate and the ester are suitably mixed in the ratio 1:0.5 to 1:2 by mole, and preferably 1:1.1 to 1:1.5 by mole.

After the transesterification reaction, the enzyme can be removed by conventional filter operation and used again, as it is. The reacted solution which is filtrate can be separated into an optically active alcohol and an ester, respectively, for instance by distillation or column chromatography. The obtained ester hydrolyzed, and the optically active compound which is an antipode of the above compound is derived.

By the above described process, the optically active R- and S-alcohol can be obtained.

The merits of this invention are as follows.

(1) Unnecessary hydrolysis of esters scarcely occurs because the transesterification reaction is substantially conducted under the conditions of no water.

(2) The enzyme can be easily recovered and reused.

(3) No special equipment and materials are used because the reaction can be performed under the conditions of relatively lower temperatures and an open system.

(4) Optically active substances having high purity are obtained by a one-step reaction.

(5) In spite of the biochemical reaction, the substrate concentration can be increased and big reaction vessels are unnecessary, because a buffer solution and the like are not required in the reaction.

DESCRIPTION OF PREFERRED EMBODIMENTS

The following examples illustrate this invention more specifically, but the present invention is not limited in these examples.

EXAMPLE 1

Three grams of enzyme (produced by Amano pharmaceutical Co. Ltd., Lipase "Amano" P), 7.3 g (0.059 mol) of (R,S)-1-(4-pyridyl)ethanol and 19.7 g (0.065 mol) of tributyrin were charged into a three-necked flask and reacted with stirring for six days at 35° C. After the reaction was stopped, the enzyme was removed by filtration, the filtrate was concentrated by distillation under reduced pressure, and the desired compounds were isolated by column chromatography. As the result, 3.0 g of S—(—)-1-(4-pyridyl)ethanol (yield: 82.6%, $[\alpha]_D = -26.6°$ (C=1.0, EtOH)) and R-1-(4'-pyridyl)ethyl butyrate were obtained. The obtained R-1-(4'-pyridyl)ethyl butyrate was hydrolyzed by alkali, and 1.8 g of R-(+)-1-(4-pyridyl)ethanol (yield: 49.5%, $[\alpha]_D = +32.4°$ (C=1.0, EtOH)) was obtained.

The obtained compounds were identified by structure analysis with NMR and by measurement of the optical rotation.

EXAMPLE 2

An enzyme 3.4 g (produced by Amano pharmaceutical Co. Ltd., Lipase "Amano" P), 8.4 g (0.068 mol) of (R,S)-1-(3-pyridyl)ethanol and 22.7 g (0.075 mol) of tributyrin were charged into a three-necked flask and reacted with stirring for 16 days at 35° C. After the reaction was stopped, the enzyme was removed by filtration, the filtrate was concentrated by distillation under reduced pressure, and the desired compounds were isolated by column chromatography. As the result, 4.3 g of S-(—)-1-(3-pyridyl)ethanol (yield: 102.7%, $[\alpha]_D = -25.0°$ (C=1.0,EtOH)) and R-1-(3'-pyridyl)ethyl butyrate were obtained. Furthermore, R-1-(3'-pyridyl)ethyl butyrate was hydrolyzed by alkali, and 3.6 g of R-(+)-1-(3-pyridyl)ethanol (yield: 86.0%, $[\alpha]_D = +49.3°$ (C=1.0, EtOH)) was obtained.

The obtained compounds were identified by structure analysis with NMR and by measurement of the optical rotation.

EXAMPLE 3

An enzyme 3.9 g (produced by Amano pharmacetical Co. Ltd., Lipasde "Amano" P), 9.7 g(0.079 mol) of (R,S)-1-(2-pyridyl)ethanol and 26.2 g(0.087 mol) of tributyrin were charged into a three-necked flask and reacted with stirring for 16 days at 35° C. After the reaction was stopped, the enzyme was removed by filtration, the filtrate was concentrated by distillation under reduced pressure, the desired compounds were isolated by column chromatography. As the result, 2.59 g of S-(—)-1-(2-pyridyl)ethanol (yield: 72.8%, $[\alpha]_D = -23.0°$ (C=1.0, EtOH) and R-1-(2'-pyridyl)ethyl butyrate were obtained. Furthermore, R-1-(2'-pyridyl)ethyl butyrate was hydrolyzed by alkali, and 3.54 g of R-(+)-1-(2-pyridyl)ethanol (yield: 53.2%, $[\alpha]_D = +45.0°$ (C=1.0, EtOH) was obtained.

The obtained compounds were identified by structure analysis with NMR and by measurement of the optical rotation.

The compounds obtained by Examples 1–3 are useful as the starting materials in the preparation of the compounds of the formula:

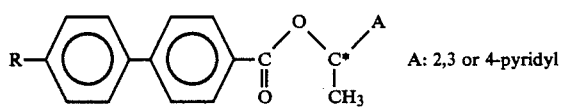

These compounds are useful as dopants which give spiral structures for liquid crystal molecules in liquid crystal compositions.

Further, a compound by Example 2 can be useful as a starting material of compound (II) which is an intermediate of an akuamidine (III, pharmacologically interesting alkaloid; J. Am. Chem. Soc., 101, 6742 (1979), M. R. Uskovic, et al.)

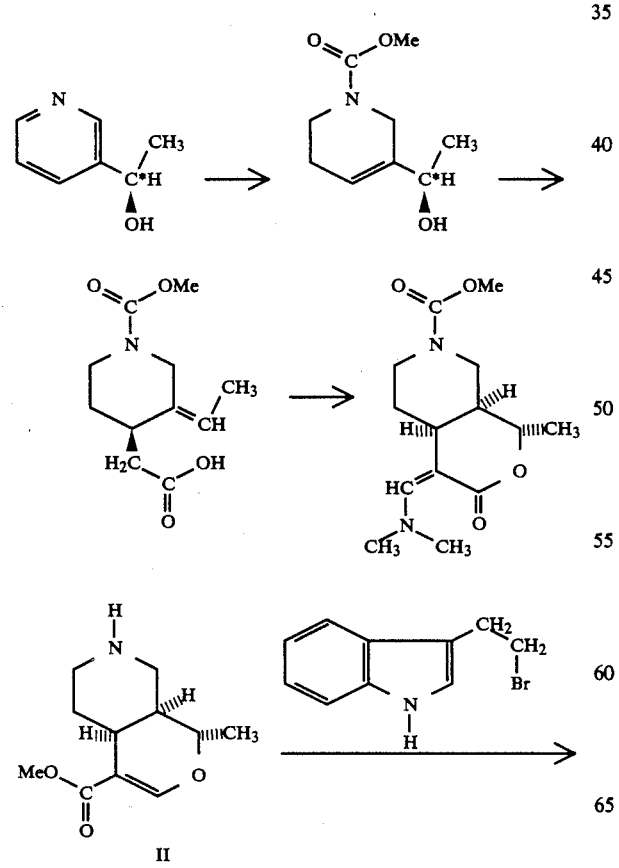

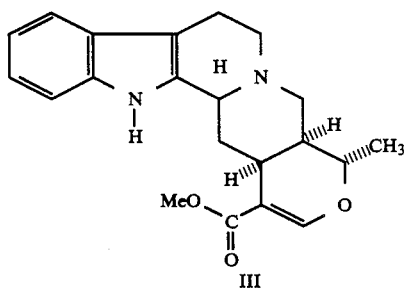

We claim:
1. A process for producing an optically active compound having a pyridine skeleton which comprises using a hydrolyase having the ability to preferentially catalyse a transesterification reaction between an R- or S- alcohol and an ester when the hydrolase is used with the (R,S)-alcohol, reacting under substantially anhydrous conditions an ester and an (R,S)-compound represented by the general formula

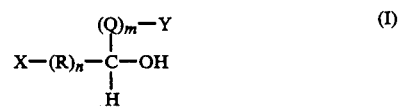

wherein X is a member selected form groups of the following formulas,

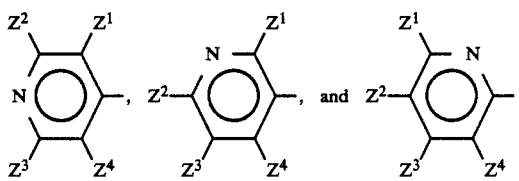

wherein each of $Z^1$, $Z^2$, $Z^3$ and $Z^4$ is a member selected from the group consisting of hydrogen and a halogen atom, a cyano group, a trifluoromethyl group, an amino group, an alkylamino group, an alkyl and an alkoxy group said group having 1-20 carbon atoms, and a group of the following formula:

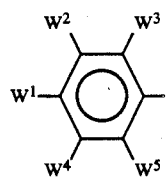

wherein each of $W^1$, $W^2W^3$, $W^4$, and $W^5$ is a member selected from the group consisting of hydrogen and a halogen atom, a cyano group, a trifluoromethyl group, an amino group, an alkylamino group, and an alkyl and an alkoxy group said groups having 1-20 carbon atoms;

Y is a member selected from the group consisting of hydrogen and a halogen atom, a cyano group, and a trifluoromethyl group;

R is an alkylene group having 1-20 carbon atoms; n is 0 or 1;

Q is an alkylene group having 1-20 carbon atoms; and m is 0 or 1;

to effect a transesterification reaction, and resolving to an optically active compound which contains richly either the R- or S-compound and correspondingly the ester of the S- or R-compound.

2. A process as claimed in claim 1, wherein the hydrolase is Lipase AP originated from *Aspergillus niger*, Lipase M from *Mucor javanicus*, Lipase P from *Pseudomonas fluorescens*, Lipase CES from *Pseudomonas sp*, Lipase CE from *Humicola lanuginosa*, Lipase F-AP from *Rhizopus javanicus*, Lipase II from *Porcine pancreas*, Lipase VIII from *Geotrichum candidum*, Lipase X from *Rhizopus delamar*. Lipase from *Chromobacterium viscosum*, Paratase A from *Aspergillus niger*, or Lipase from *Rhizopus niveus*.

3. A process as claimed in claim 2, wherein the hydrolase is Lipase P originated from *Pseudomonus fluorescens*.

4. A process as claimed in claim 1, wherein the starting ester is a triglyceride.

5. A process as claimed in claim 4, wherein the triglyceride is tributyrin.

6. A process as claimed in claim 1, wherein X is a 4-pyridyl group, Y is a hydrogen atom, Q is a methylene group and n is 0.

7. A process as claimed in claim 1, wherein the starting compound represented by the formula (I) is (R,S)-1-(4-pyridyl)ethanol.

8. A process as claimed in claim 1, wherein X is a 3-pyridyl group, Y is a hydrogen atom, Q is a methylene group and n is 0.

9. A process as claimed in claim 1, wherein the starting compound represented by the formula (I) is (R,S)-1-(3-pyridyl)ethanol.

10. A process as claimed in claim 1, wherein X is a 2-pyridyl group, Y is a hydrogen atom, Q is a methylene group and n is 0.

11. A process as claimed in claim 1, wherein the starting compound represented by the formula (I) is (R,S)-1-(2-pyridyl)ethanol.

12. A process as claimed in claim 2, wherein the starting compound represented by the formula (I) is (R,S)-1-(4-pyridyl)ethanol.

13. A process as claimed in claim 4, wherein the starting compound represented by the formula (I) is (R,S)-1-(4-pyridyl)ethanol.

14. A process as claimed in claim 2, wherein the starting compound represented by the formula (I) is (R,S)-1-(3-pyridyl)ethanol.

15. A process as claimed in claim 4, wherein the starting compound represented by the formula (I) is (R,S)-1-(3-pyridyl)ethanol.

16. A process as claimed in claim 2, wherein the starting compound represented by the formula (I) is (R,S)-1-(2-pyridyl)ethanol.

17. A process as claimed in claim 4, wherein the starting compound represented by the formula (I) is (R,S)-1-(2-pyridyl)ethanol.

* * * * *